United States Patent
Petersen et al.

(10) Patent No.: US 8,257,262 B2
(45) Date of Patent: *Sep. 4, 2012

(54) ULTRASOUND ADAPTOR METHODS AND SYSTEMS FOR TRANSDUCER AND SYSTEM SEPARATION

(75) Inventors: David A. Petersen, Fall City, WA (US); Robert N. Phelps, Sammamish, WA (US); John C. Lazenby, Fall City, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 746 days.

This patent is subject to a terminal disclaimer.

(21) Appl. No.: 10/741,538

(22) Filed: Dec. 19, 2003

(65) Prior Publication Data

US 2005/0148873 A1    Jul. 7, 2005

(51) Int. Cl.
  *A61B 8/00* (2006.01)
(52) U.S. Cl. ........................ 600/459; 600/437
(58) Field of Classification Search .................. 600/459, 600/437
  See application file for complete search history.

(56) References Cited

U.S. PATENT DOCUMENTS

| | | | |
|---|---|---|---|
| H001171 H * | 4/1993 | Fillhart et al. | 181/125 |
| 5,267,221 A | 11/1993 | Miller et al. | |
| 5,348,014 A * | 9/1994 | Okado | 600/445 |
| 5,406,949 A | 4/1995 | Yao et al. | |
| 5,522,393 A | 6/1996 | Phillips et al. | |
| 5,538,004 A | 7/1996 | Bamber | |
| 5,555,534 A | 9/1996 | Maslak et al. | |
| 5,562,097 A | 10/1996 | Yao | |
| 5,573,001 A * | 11/1996 | Petrofsky et al. | 600/447 |

(Continued)

FOREIGN PATENT DOCUMENTS

CN    1342442 A    4/2002

(Continued)

OTHER PUBLICATIONS

"Fully Sampled Matrix Transducer for Real Time 3D Ultrasonic Imaging," by Bernard Savord, Rod Solomon—Philips Medical Systems, 300 Minuteman Rd., Andover MA; 9 pgs.; before Dec. 2003.

*Primary Examiner* — Jacqueline Cheng (57) ABSTRACT

Methods and systems are provided for adapting signals from an ultrasound transducer for an ultrasound system. Where the signal processing in a transducer assembly outputs data incompatible with the ultrasound system, circuitry provided within the transducer assembly converts the data to be compatible with the ultrasound systems. For example, sub-array mixing is provided to partially beamform signals from a plurality of transducer elements. The resulting output signals from a plurality sub-arrays are provided through a cable to a connector housing of the transducer probe assembly. Since the mixers alter the data, such as shifting the data to an intermediate frequency, the output data may be at a frequency different than the frequencies for operation of the receive beamformer. Additional mixers are then provided to convert the intermediate frequency signals to radio frequency signals that may be processed by the ultrasound systems received beamformer. As another example, signals from a plurality of transducer elements are multiplexed together. Where the receive beamformer is not operable to de-multiplex such signals, circuitry within the transducer probe assembly converts the signals by de-multiplexing the data for beamforming. Ultrasound systems have a limited number of received beamformer channels. By providing signal processing, conversion, and/or partial beamforming within the transducer probe assembly, the number of elements used may be different than the number of received beamformer channels provided by the system.

21 Claims, 3 Drawing Sheets

U.S. PATENT DOCUMENTS

| | | | |
|---|---|---|---|
| 5,590,658 A | 1/1997 | Chiang et al. | |
| 5,617,866 A | 4/1997 | Marian, Jr. | |
| 5,622,177 A * | 4/1997 | Breimesser et al. | 600/459 |
| 5,627,536 A | 5/1997 | Ramirez | |
| 5,676,147 A | 10/1997 | Petrofsky et al. | |
| 5,678,551 A | 10/1997 | Stevens | |
| 5,690,114 A | 11/1997 | Chiang et al. | |
| 5,817,024 A | 10/1998 | Ogle et al. | |
| 5,820,549 A | 10/1998 | Marian, Jr. | |
| 5,839,442 A | 11/1998 | Chiang et al. | |
| 5,957,846 A | 9/1999 | Chiang et al. | |
| 5,964,709 A | 10/1999 | Chiang et al. | |
| 5,997,479 A | 12/1999 | Savord et al. | |
| 6,013,032 A * | 1/2000 | Savord | 600/443 |
| 6,016,285 A | 1/2000 | Wright et al. | |
| 6,029,116 A * | 2/2000 | Wright et al. | 702/32 |
| 6,102,863 A | 8/2000 | Pflugrath et al. | |
| 6,106,472 A | 8/2000 | Chiang et al. | |
| 6,126,602 A | 10/2000 | Savord et al. | |
| 6,126,606 A | 10/2000 | Bergstoel | |
| 6,142,946 A | 11/2000 | Hwang et al. | |
| 6,248,073 B1 | 6/2001 | Gilbert et al. | |
| 6,371,918 B1 | 4/2002 | Bunce | |
| 6,375,617 B1 * | 4/2002 | Fraser | 600/443 |
| 6,491,634 B1 * | 12/2002 | Leavitt et al. | 600/447 |
| 6,527,722 B1 | 3/2003 | Fazioli et al. | |
| 6,530,887 B1 | 3/2003 | Gilbert et al. | |
| 6,537,219 B2 | 3/2003 | Poland et al. | |
| 6,540,685 B1 | 4/2003 | Rhoads et al. | |
| 6,544,175 B1 * | 4/2003 | Newman | 600/437 |
| 6,575,908 B2 | 6/2003 | Barnes et al. | |
| 6,582,367 B1 | 6/2003 | Robinson et al. | |
| 6,589,179 B2 | 7/2003 | Criton et al. | |
| 6,612,987 B2 | 9/2003 | Morsy et al. | |
| 6,629,928 B1 | 10/2003 | Dolan et al. | |
| 6,635,019 B2 | 10/2003 | Davidsen | |
| 6,648,826 B2 | 11/2003 | Little et al. | |
| 6,752,763 B2 * | 6/2004 | Erikson | 600/459 |
| 6,814,701 B1 | 11/2004 | Tamura | |
| 6,875,178 B2 | 4/2005 | Phelps et al. | |
| 6,932,517 B2 | 8/2005 | Swayze et al. | |
| 7,169,108 B2 | 1/2007 | Little et al. | |
| 7,371,218 B2 | 5/2008 | Walston et al. | |
| 2002/0081871 A1 * | 6/2002 | Swayze et al. | 439/76.1 |
| 2003/0139664 A1 * | 7/2003 | Hunt et al. | 600/407 |
| 2003/0171674 A1 * | 9/2003 | Jago et al. | 600/437 |
| 2004/0002657 A1 * | 1/2004 | Marian | 600/459 |
| 2004/0015079 A1 | 1/2004 | Berger et al. | |
| 2004/0109028 A1 | 6/2004 | Stern et al. | |
| 2004/0181154 A1 * | 9/2004 | Peterson et al. | 600/459 |
| 2005/0148878 A1 | 7/2005 | Phelps et al. | |
| 2005/0192499 A1 | 9/2005 | Lazenby | |
| 2005/0203391 A1 | 9/2005 | Phelps et al. | |
| 2005/0203404 A1 | 9/2005 | Freiburger | |
| 2008/0027322 A1 | 1/2008 | Freiburger | |
| 2008/0027323 A1 | 1/2008 | Freiburger | |

FOREIGN PATENT DOCUMENTS

| | | |
|---|---|---|
| EP | 1049407 B1 | 12/2005 |
| WO | WO 00/30540 | 6/2000 |

\* cited by examiner

FIG.5

ULTRASOUND ADAPTOR METHODS AND SYSTEMS FOR TRANSDUCER AND SYSTEM SEPARATION

BACKGROUND

The present invention relates to transducer architectures and ultrasound systems. In particular, electronics are positioned in an ultrasound transducer probe assembly.

Medical diagnostic ultrasound systems typically have detachable ultrasound probe assemblies. A transducer array is housed in a hand-held probe. The hand-held probe is connected through a cable to a connector housing. The connector housing electrically and mechanically releasably connects to an ultrasound system. The user can select different ultrasound probes for different examinations and connect the selected probe to the ultrasound imaging system. Using beamformers and other circuitry in the ultrasound imaging system, an image is generated through the transmission and reception of acoustic energy by the connected transducer probe.

Electronics associated with the imaging system have been placed in the ultrasound probe housing. For example, time delays and summers are positioned in a transducer probe to perform partial beamforming from a multidimensional array. The partially beamformed signals (i.e., signals from each beamformed sub-array) are output to the ultrasound imaging system for beamforming. As another example, U.S. Pat. No. 5,590,658 discloses a hand-held probe housing in which the ultrasonic transducers and beam forming circuitry are housed. As another example, U.S. Pat. No. 6,875,178(U.S. application Ser. No. 10/184,461), the disclosure of which is incorporated herein by reference, discloses integrating a multiplexer and other electronics in the hand-held ultrasound transducer probe housing. Signals from a plurality of transducer elements are time division multiplexed onto a few number of cables for transmission to the ultrasound imaging system. In another ultrasound transducer probe assembly, a controller for a wobbler transducer is positioned in the connector housing for controlling the motor of the wobbler array in the probe housing. As yet another example, switches for selecting an aperture on a 1.5 D array or passive tuning inductors are positioned within a connector housing of a transducer assembly.

BRIEF SUMMARY

By way of introduction, the preferred embodiments described below include methods and systems for adapting signals from an ultrasound transducer for an ultrasound system. For real time, three-dimensional imaging or other imaging, partial beamforming or other signal processes are performed within an ultrasound transducer assembly. Where the processes result in data incompatible with the ultrasound system, circuitry provided within the transducer assembly converts the data to be compatible with the ultrasound system. For example, sub-array mixing is provided to partially beamform signals from a plurality of transducer elements. The mixers and summers are provided in the transducer probe. The resulting output signals are provided through a cable to a connector housing of the transducer probe assembly. Since the mixers alter the data, such as shifting the data to an intermediate frequency, the output data may be at a frequency different than the frequencies for operation of the receive beamformer. Additional mixers are then provided to convert the intermediate frequency signals to radio frequency signals that may be processed by the receive beamformer. As another example, signals from a plurality of transducer elements are multiplexed together, such as using time divisional diplexing. Where the received beamformer is not operable to de-multiplex such signals, circuitry within the transducer probe assembly converts the signals by de-multiplexing the data. Ultrasound systems have a limited number of received beamformer channels. By providing signal processing, conversion, and/or partial beamforming within the transducer probe assembly, the number of elements used may be different than the number of receive beamformer channels provided by the system.

Since the signal processing electronics in the ultrasound transducer probe assembly may output data different than usable by the received beamformer, a full bandwidth of the coaxial cable may be utilized between the probe housing and the connector housing. Optical fibers or other cables may be used as an alternative to coaxial cables. This signaling format between the probe housing and the connector housing is unconstrained by the number and compatibility of receive beamformer channels. Any of different transducer array technologies may be used, including PZT, CMUT or multi-layer PZT. Where a new technology is developed, the ultrasound transducer probe assembly is used to convert signals from the new technology to signals expected by the receive beamformer. By providing some or all of the electronics discussed herein within the connector housing, power dissipation, thermal dissipation and the volume available for electronics may be larger than positioning the electronics within the transducer probe housing. Other, different or none of the above advantages may be provided while using one or more aspects, systems or methods claimed below.

In a first aspect, a method for adapting signals from an ultrasound transducer for an ultrasound system is provided. Signals from a plurality of elements are processed within a transducer assembly. The processed signals are converted to a different form appropriate for the ultrasound system. The conversion is performed in the transducer assembly.

In a second aspect, a transducer assembly for adapting signals from an ultrasound transducer for an ultrasound system is provided. A cable connects with the ultrasound transducer. A connector housing at least partially encloses a detachable connector and a signal processing device. The cable electrically connects elements of the ultrasound transducer to the signal processing device. The detachable connector is operable to connect and disconnect from the ultrasound system. The detachable connector is also operable to output signals responsive to the signal processing device and the ultrasound transducer.

In a third aspect, a method for adapting signals from an ultrasound transducer for an ultrasound system is provided. Signals from a plurality, M of elements of an ultrasound transducer are partially beamformed. The partial beamforming is performed in the transducer assembly. The partially beamformed signals are converted to a different form appropriate for the ultrasound system. The conversion is performed in the transducer assembly. The converted, partially beamformed signals are output to a plurality, N, of beamformer channels of the ultrasound system. N is less than M.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and figures are not necessarily to scale, emphasis instead being placed upon illustrating the principles

DETAILED DESCRIPTION OF THE DRAWINGS AND PRESENTLY PREFERRED EMBODIMENTS

Many of the devices and associated processing within the transducer assembly discussed below may be performed anywhere within the transducer assembly. In one embodiment, some or all of the electronics are positioned within a connector housing where space and power are more readily available as opposed to a transducer probe housing or along a cable. Signals that are incompatible with the receive beamformer of an ultrasound imaging system are converted into compatible signals. For example, many current ultrasound systems are unable to accept signals outside of a certain frequency range, digital signals or multiplexed signals. Electronics within the transducer assembly, such as the connector housing, convert digital signals to analog, multiplexed signals to de-multiplexed signals, or signals at one frequency band shifted to another frequency band. As a result, state of the art circuit technology may be provided within the transducer probe assembly for partial beamforming, compressing or otherwise processing data from a transducer array. These processes may be independent of a form of signals usable by the received beamformer of an old, conventional or incompatible ultrasound system. The number of cables connecting a transducer array to an ultrasound system and the signaling scheme used on the cables may be selected independent of the receive beamformer of the imaging system. Partial beamforming may alter the data in ways that would not be compatible with the receive beamformer. The positioning of signal processing circuitry within the connector housing of the transducer probe assembly, partial beamforming followed by conversion to a compatible format, or other processing of signals within a transducer assembly followed by converting the processed signals to a compatible format may be used independently of each other or in any combination.

Figure 1:
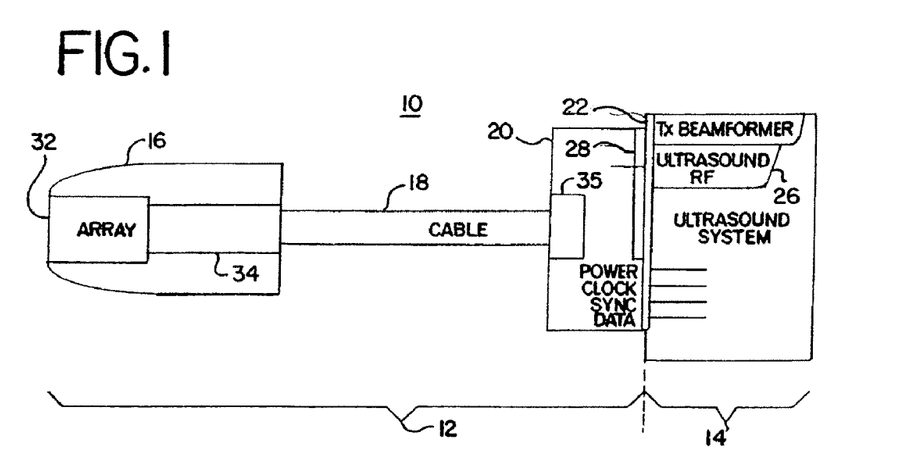
FIG. 1 is a block diagram of a transducer assembly in an ultrasound imaging system in one embodiment.

FIG. 1 shows one embodiment of a system 10 with a transducer assembly 12 for adapting signals from an ultrasound transducer array 32 for an ultrasound system 14. FIG. 1 shows the transducer assembly 12 connected to the ultrasound system 14. The detachable transducer assembly 12 allows selection of different transducers with different frequency responses or other characteristics for imaging by the ultrasound system 14.

The ultrasound system 14 is a medical diagnostic ultrasound imaging system in one embodiment. In other embodiments, the ultrasound system 14 is a computer, work station or other medical imaging system. For a stand alone ultrasound system, the ultrasound system 14 includes a transmit beamformer 24 and a receive beamformer 26 connected with a connector 22. The transmit beamformer 24 is operable to generate a plurality of relatively delayed and apodized waveforms for transmitting acoustic energy along one or more beams at the same time. The electrical signals generated by the transmit beamformer 24 are routed to the connector 22. The connector 22 also electrically connects to the receive beamformer 26. In one embodiment, the connections within the ultrasound system 14 from the connector 22 are permanent and made through one or more switches, such as a transmit and receive switch.

The receive beamformer 26 is an analog or digital receive beamformer. The receive beamformer 26 is configured to receive analog signals at a radio frequency band (e.g., a band centered at 2-10 MHz), but may be configured to receive either analog or digital signals at the same or different frequency bands. In one embodiment, the receive beamformer 26 includes separate beamformers for different imaging modes, such as a separate spectral Doppler beamformer and a B-mode and color-flow mode beamformer. For example, the receive beamformer 26 is a processor on a printed circuit board, ASIC or other device. The beamformer 26 includes a plurality of delays, amplifiers and one or more summers. The electrical signals representing different elements or groups of elements are relatively delayed, apodized and then summed to form samples or signals representing different spatial locations along one or more receive beams. The beamformers 24, 26 are configured to provide a wideband interface, such as a switching matrix with 128, 192 or 384-wire impedance controlled paths from the connector 22 to the beamforming cards or slots on the printed circuit board interconnects. Other switching matrix and number of paths may be provided.

Further processes and associated circuitry are implemented by the ultrasound system 14 for generating an image or for calculating measurements from the receive beamformed information. Different, additional or fewer transmit and receive circuit devices or components may be provided.

The transmit beamformer 24, receive beamformer 26 and connector 22 are at least partially enclosed within a system housing 25. The system housing 25 is plastic, metal, wood, fiberglass, or any other now-known or later-developed material for housing electronics. In one embodiment, the system housing 25 is a workstation or cart-based housing supported on wheels or resting on the floor. In other embodiments, the system housing 25 is a lap top or other portable-sized device, such as a suitcase-sized portable ultrasound system. In yet another embodiment, the system housing 25 is a hand-held ultrasound system, such as a PDA or scope-shaped housing.

The connector 22 is one of any now-known or later-developed mechanical and electrical connectors for detachably connecting and removing the transducer assembly 12. The connector 22 includes grooves, extensions, latches, screws, threaded holes or any other now-known or later-developed mechanical structure for releasably connecting to another device. A plurality of male or female electrical connections for connecting with individual digital traces, such as in a circuit board configuration, or for connecting with coaxial cables is provided. For example, 192 or other number of electrical connections of exposed metallic traces on a circuit board for mating are recessed within the connector 22. In one embodiment, the connector disclosed in U.S. Pat. No. 6,371, 918, the disclosure of which is incorporated herein by reference, is used.

The connector 22 mounts to the system housing 25. While one connector 22 is shown, a plurality of different connectors may be provided for connecting to a same type or different types of transducer probe assemblies 12. The connector 22 electrically connects with the receive beamformer 26. In alternative embodiments, the connector 22 is a standard or custom connection on a PC, digital repeater or other electrical device for locally processing data or for transmitting data for remote processing.

In one embodiment, the connector 22 includes one or more switches, such as a multiplexer, group of transistors or other switching device for switching one or more inputs from the connector 22 to different receive beamformers or different channels of a given receive beamformer 26. In other embodiments, the switch for switching between receive beamformers or channels is provided by components separate from the connector 22 or is not provided.

The ultrasound transducer assembly 12 includes a transducer probe housing 16, a cable 18, and a connector housing 20. Additional, different or fewer components may be provided. For example, a hand-held system 10 is provided where the transducer probe housing 16 is included as part of the connector housing 20 without the cable 18. The transducer assembly 12 provides a detachable transducer for connecting and disconnecting from the ultrasound system 14.

The transducer probe housing 16 is plastic, metal, rubber, combinations thereof or any other now-known or later-developed material for housing a transducer array of elements 32. In one embodiment, the transducer probe housing 16 is shaped for hand-held use. In other embodiments, the transducer probe housing 16 is shaped for use internal to a patient, such as shaped as an endoscope or catheter. The transducer probe housing 16 at least partially houses an array of elements, such as covering a portion of the array and allowing a face of the array acoustical access for scanning a patient.

The array of elements 32 is an array of piezoelectric, multilayer piezoelectric, capacitive membrane ultrasound transducer or other now-known or later-developed elements for converting between electrical and acoustical energies. One or multidimensional arrays are provided with full or sparse sampling. For example, a 2-dimensional array has M elements (e.g., 1,920 or other number) fully-sampled in a square or rectangular grid positioned on a planar or curved surface. The transducer array 32 includes a flex circuit, signal traces or other structures for electrical interconnection from the elements of the array 32 to other electronics of the probe assembly 12. For example, the flex circuits are connected to a plurality of coaxial cables in the cable 18 or to electronics within the connector housing 20.

In an alternative embodiment, the transducer array 32 electrically connects to electrical components 34 within the probe housing 16. For example, the probe electronics 34 include a multiplexer electrically connected between the plurality of cables of the cable 18 and the transducer elements of the array 32. The multiplexer is positioned in the transducer probe housing 16 with the array 32. The multiplexer is operable to multiplex signals from a plurality of elements onto a fewer number of outputs using time division multiplexing. In alternative embodiments, other forms of multiplexing are provided. Preamplifiers or other structures are also included in other embodiments with the multiplexer. For example, the structures disclosed in U.S. Pat. Nos.6,875,178 and 7,371, 218(U.S. Ser. Nos. 10/184,461 and 10/341,871), the disclosures of which are incorporated herein by reference, are used. For a multidimensional array, signals from every 2, 4, 8 or other number of elements are multiplexed onto a common analog or digital output. A plurality of outputs for different groups of elements is provided.

In another embodiment, the probe electronics 34 include delays, amplifiers and summers for performing beamforming functions for sub-arrays or across the entire array. For example, time based delays and summers are provided for sub-array or partial beamforming. As yet another example, sub-array mixing is used for partial beamforming. Using mixers (e.g., multipliers), different phase adjustments are applied to signals from different elements. This phase adjustment approximates a delay, but may result in shifting the frequency of the signals to an intermediate frequency. The phase adjustment may also alter the data to be a mirror image in spectral content. The phase adjusted signals for each sub-array are then summed by a summer. U.S. Pat. No. 5,573,001, the disclosure of which is incorporated herein by reference, shows different embodiments for sub-array mixing. The circuits for the sub-array mixing are in the transducer assembly 12, such as in the probe housing 16.

In alternative embodiments, the probe electronics 34 are different components for the same or different functions, or the transducer probe housing 16 is provided without the further electronics 34. Other signal processing using active components may be provided, such as filtering or amplifying.

The cable 18 includes a plurality of coaxial cables connected with the ultrasound transducer array 32. For example, 64, 128, 192 or other number of coaxial cables are provided for transmitting electrical signals representing acoustic energy received at elements of the array 32. Each coaxial cable receives information for one element or information representing a plurality of different elements. In alternative embodiments, the cable 18 is a flexible circuit, optical data path, fiber optic, insulated wires or other now-known or later-developed structure. For example, analog-to-digital converters are provided in the transducer probe housing 16, and digital signals are transmitted along now-known or later-developed digital paths through the cable 18. The cable 18 electrically connects the ultrasound transducer array 32 to the electronics of the connector housing 20. Where multiplexing or partial beamforming is provided, fewer cables than elements may be used.

The connector housing 20 is metal, plastic, rubber, combinations thereof or other now-known or later-developed materials for housing or at least partially enclosing a signal processing device 35 and a detachable connector 28. Additional, different or fewer components may be included within the connector housing 20. For example, termination resistors or passive tuning circuits connect with each of the cables for providing an impedance match. The transmit path is provided by switches (e.g., multiplexer or transistor) to bypass the signal processing of the receive circuitry and connect to the cable 18. Alternatively, a portion or all of the transmit beamformer is provided within the transducer assembly 12. Controllers or other now known or later developed active or passive devices may be provided. As another example, a part or all of the signal processing device 35 is positioned within the probe housing 16 or cable 18 rather than the connector housing 20. The connector housing 20 is connected at the end of the cable 18, so that the connector housing 20 is spaced from the ultrasound transducer array 32 and associated probe housing 16.

The connector housing 20 is shaped to allow detachment and attachment to the housing 25 of the ultrasound system 14. In one embodiment, now-known connector housings are extended in length away from the connector 28 to accommodate the additional electronics, such as extending by twice the distance used for connectors without electronics. Different changes in dimension may be provided, such as making the connector housing 20 longer, higher, wider or combinations thereof. The connector housing 20 is shaped and sized to include heat sinking, fans and/or active cooling for cooling the enclosed electronics. In alternative embodiments, no additional cooling devices or different now-known or later-developed cooling is provided. In one embodiment, at least one fan is positioned adjacent to a vent in the connector housing 20. Additionally or alternatively, a rigid thermal connection is provided between the connector housing 20 and the ultrasound system 14 for conducting heat away from the electronics. A forced air connection between the connector housing 20 and the ultrasound system 14 may alternatively be provided for ducting hot air from the connector housing 20 through a fan in the ultrasound system 14 or forcing air from the ultrasound system 14 into the connector housing 20.

Figure 2:
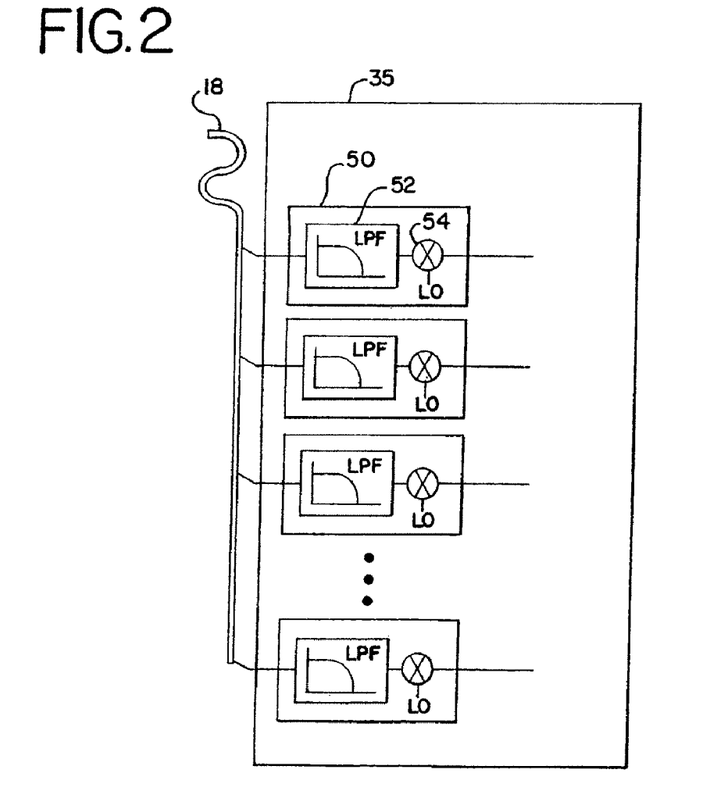
FIG. 2 is a block diagram of one embodiment of a signal processing device.
Figure 3A:
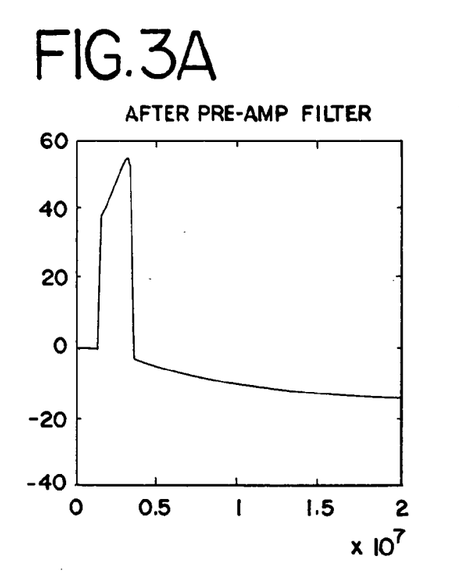
FIGS. 3A-D are graphical representations of an example partial beamforming process using sub-array mixing.
Figure 3B:
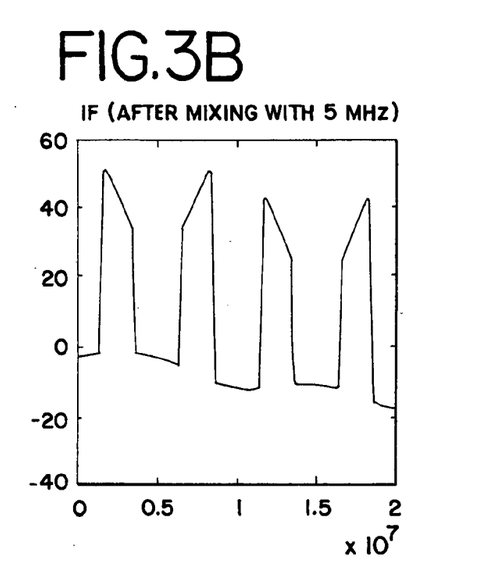
Figure 3C:
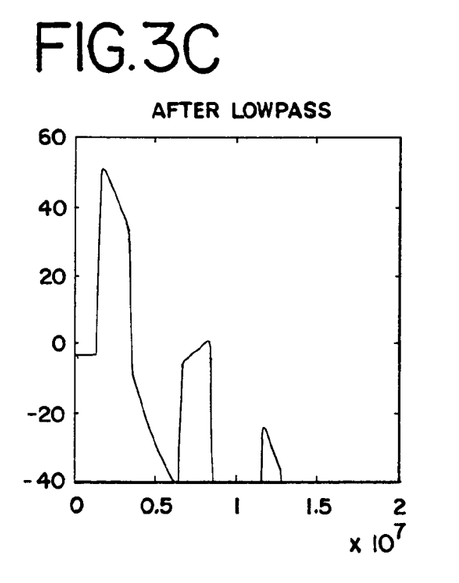
Figure 3D:
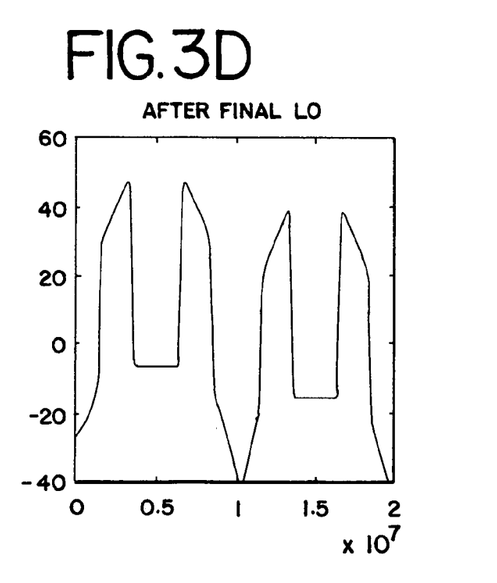
Figure 4:
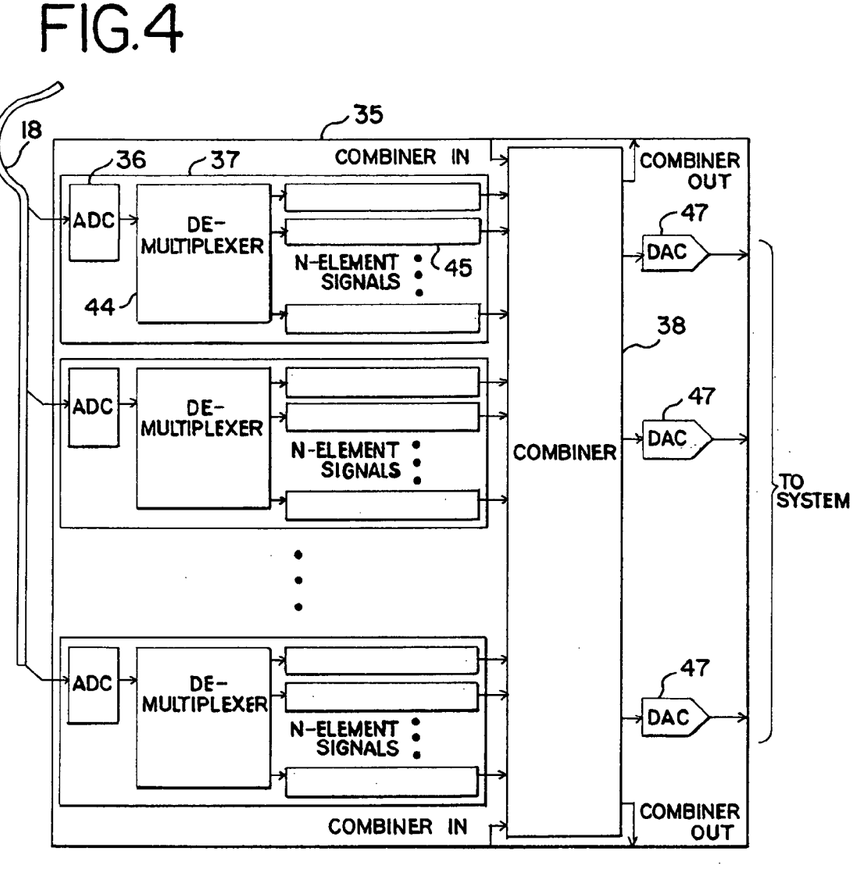
FIG. 4 is a block diagram of one embodiment of a signal processing circuit.

The signal processing device 35 is a filter, analog-to-digital converter, digital-to-analog converter, mixer, multiplier, demultiplexer, summer, digital circuit, analog circuit, application specific integrated circuit, general processor, digital signal processor, combinations thereof or other now know or later developed device for actively processing signals from one or more elements of the array 32. In one embodiment, a portion or the entire signal processing device 35 is enclosed within the probe housing 16. For example, the signal processing device 35 is the electronics 34 for partial beamforming, multiplexing or performing other signal processing. In another embodiment, the cable 18 electrically connecting the elements of the ultrasound transducer array 32 to the signal processing device 35 where the signal processing device 35 is enclosed within the connector housing 20. For example, the signal processing device 35 includes circuits or devices for converting signals to a different form appropriate for the receive beamformer 26 of the ultrasound system 14. FIGS. 2 and 4 show two embodiments of the signal processing device 35 for converting processed signals, one embodiment for converting sub-array mixed signals (FIG. 2) and another for converting multiplexed signals (FIG. 4).

As shown in FIG. 2, the signal processing device 35 includes a plurality of mixing circuits 50. Each mixing circuit 50 includes a low pass filter 52 and a multiplier 54, but additional, different or fewer components may be provided. For example, a gain-control device is useful for matching the output signal amplitude with the input of the ultrasound system 20. Such a gain control device may have fixed or time-varying gain. A mixing circuit 50 is provided for each of the sub-arrays. For example, a multi-dimensional transducer array 32 is used for real time three-dimensional imaging. Signals for different groups of elements are mixed with different phasing and summed to form signals for a plurality of different sub-arrays. A mixing circuit 50 is then provided for each of the sub-array signals. The low pass filter 52 comprises a plurality of passive analog components for removing the added signal components at different harmonic frequencies. In alternative embodiments, the low pass filter 52 is an active analog or digital circuit. For example, the mixing circuit 50 or the signal processing circuit 35 includes analog-to-digital or digital-to-analog converters for implementing the sub array mixing from the intermediate frequency back to the radio frequency using digital devices.

An example sub-array mixing scheme is shown in FIG. 3. The graphical representation after preamplification filtering of FIG. 3A represents a signal prior to sub-array mixing. After mixing with a same or different frequency signal, such as a 5 MHz mixing signal for a 2.5 MHz receive signal, a plurality of different signal components are added as shown in FIG. 3B. At 2.5 MHz, the same signal is maintained only at a mirror image. The mixed signals from a plurality of different elements are then summed together. Since the receive beamformer may not function properly in receiving a mirror image signal or a signal with a plurality of added components, the mixing circuit 50 intercepts the partially beamformed, sub-array mixed, intermediate frequency signals and uses filtering and mixing to output signals that are used with a conventional radio frequency interface of the receive beamformer 26. FIG. 3C shows the intermediate frequency signal after low pass filtering. Since the signal of interest at 2.5 MHz is still a mirror image signal, the multiplier 54 is used as a mixer to convert the intermediate frequency back to the radio frequency as well as repeating the mirror image function. The mixing frequency used by the multiplier 54 is the same frequency as used in the sub-array mixing for partial beamforming. The additional undesired frequency components, such as shown in FIG. 3D after mixing, are removed by an additional low pass filter, such as provided within the ultrasound system 14 or provided as part of the signal processing device 35. The example in FIG. 3 allows the use of a low-pass filter 52 prior to the final mixer 54. Other choices of mixing frequency may require different filtering (e.g. BPF or HPF) before and/or after the final mixer to select the desired component and reject others.

Using sub-array mixing, each of the mixing circuits 50 reverses or converts signals altered from the sub-array mixing to signals usable by the ultrasound system 14. Each mixing circuit 50 outputs the converted signals to the system connector 28 for use by the receive beamformer 26. Since the signals are converted to a different form, the low power sub-array partial beamformer using phase adjustments and summation may be provided within the transducer assembly 12. In alternative embodiments, the multiplier 54 or mixing circuit 50 alter the frequency of signals from a single element to a receive beamformer 26 compatible frequency.

FIG. 4 shows the signal processing device 35 for use with multiplexing, such as time division multiplexing. In the transducer probe housing 16, signals from different groups of elements are multiplexed together for transmission along a fewer number of cables 18 than transducer elements in the array 32. Since conventional ultrasound systems may not process multiplexed signals, the signal processing device 35 converts the signals into a form usable by the receive beamformer 26. As a result, multiplexing is provided within the transducer assembly 12 for reducing the number of cables 18 while still outputting signals to the ultrasound system 14 usable by conventional receive beamformers 26. For example, the signal processing circuitry 35 performs partial beamforming after demultiplexing of signals so that a fewer number of receive beamformer channels 26 may be used with a greater number of elements in the array 32.

The signal processing device 35 is an application specific integrated circuit, digital circuit, analog circuit, general processor, digital signal processor, combinations thereof or other now known or later developed device for processing signals. A channel 37 is provided for each of the multiplexed signal lines from the cable 18. Each channel 37 includes an analog-to-digital converter 36, a demultiplexer 44, and a plurality of signal processors 45, one for each of the demultiplexed signals or signals associated with each element of the array 32. Different, additional or fewer components may be provided for each of the channels 37. In another embodiment, analog demultiplexors 44 are used and analog-to-digital converters 36 are not used. Partial beamforming of analog demultiplexed signals may be used to drive signals into the system directly without DAC 47, or a greater number of low-speed ADCs may be used after analog demultiplexing followed by digital processing and DAC conversion. A greater or lesser number of channels 37 may be provided for the same number of multiplexed signal lines of the cable 18.

The analog-to-digital converters 36 are processors, application-specific integrated circuits, digital components, analog components, amplifiers, transistors, combinations thereof or other now-known or later-developed devices for converting analog information to digital samples. One analog-to-digital converter 36 is provided for each of the signal lines of the cable 18, or one analog-to-digital converter 36 may be used for multiple of the signal lines. Any number of bits of resolution may be provided by the analog-to-digital converter, such as 4, 8 or 10-bits. Any sampling rate may be used, such as sampling at four times the center frequency of the transducer array 32 on a time-division multiplexed output line (e.g., 96 megasamples per second). In one embodiment, each analog-to-digital converter 36 is a single device or is a package or chip including analog-to-digital converters 36 for 16 to 32 time-division multiplexed channels. At 32 channels per chip, 256 channels of analog-to-digital conversion are provided by 8 devices. Each chip may have 672 pins and be 45 mm on a side with a die size of 12.8 by 12.8 mm. Other size chips and associated analog-to-digital conversion structures may be used. The analog-to-digital converters 36 connect between the ultrasound transducer array 32 and the detachable connector 28. Each of the analog-to-digital converters 36 whether in a same or different chip connects with different ones of the plurality of transducer elements. For example, one analog-to-digital converter 36 connects with one element. As another example, one analog-to-digital converter 36 connects with a group of elements with time-division multiplexed signals output on a same line. Different analog-to-digital converters 36 connect with different elements or groups of elements. To reduce power consumption of a plurality of analog-to-digital converters 36, a slightly lower than rated sampling rate may be used, but a full sampling rate may be provided, such as providing for 10-bit sampling at 120 megasamples per second with a power dissipation of about 50 milliwatts.

The demultiplexers 44 are application-specific integrated circuits, multiplexers or other now-known or later-developed devices for demultiplexing time division or other multiplexed information. The demultiplexers 44 connect with the output of the analog-to-digital converters 36 for providing signals representing specific single or small groups of elements separately. In alternative embodiments, the demultiplexers 44 are positioned prior the analog-to-digital converters 36 or not provided. The signal processors 45 may be used, for example, for filtering, mixing or delaying the signals.

The combiner 38 is an application-specific integrated circuit, transistors, multiplexer, switches, delays, amplifiers, summers, digital circuit, analog circuit, combinations thereof or other now-known or later-developed digital signal processing device. In one embodiment, the combiner 38 together with the signal processors 45 provide partial beamforming, such as where the number of elements of the transducer array 32 is greater than the number of separate electrical connections between the connector 28 and the connector 32 of the ultrasound system 14. The combiner 38 is connected between the analog-to-digital converters 36 and the electrical outputs of the connector 28. Digital data is provided as an input for processing, such as partial beamforming operable to combine data from elements of the transducer array and output the combined data on respective ones of the plurality of electrical outputs of connector 28. For example, data from sub-arrays of elements are combined and output as a single data stream. Separate data streams are output for different elements or sub-arrays. The partial beamformer implemented by the combiner 38 connects with the analog-to-digital converters 36 to combine signals from at least two elements of the transducer array 32. By compressing the data, the number of transducer elements used may be independent of the number of system connections or channels of the ultrasound system 14. Alternatively, the multiplexed signals include previous partial beamforming, so the signal processing device 35 demultiplexes without or with further partial beamforming. Demultiplexing may be used free of prior or subsequent partial beamforming in the transducer assembly 12.

In one embodiment, the combiner 38 includes multiple devices and interconnected signal lines to connect multiple combiners 38 for expansion. The interconnected signal lines allow signals from different elements to be combined regardless of the particular combiner 38 connected with the signals. While one input channel 37 is shown for each output of the combiner 38, a different number (e.g., more or less) of outputs than input channels 37 may be provided.

The digital-to-analog converters 47 are processors, application specific integrated circuits, digital components, analog components, amplifiers, transistors, combinations thereof or other now known or later developed devices for converting digital information into analog signals. One digital-to-analog converter 47 is provided for each of the output lines of the combiner 38 and for each of the receive beamformer channels used in any given receive beamformer aperture. Any of now known or later developed coding schemes for the digital-to-analog converter 47 may be used. The digital-to-analog converters 47 output to the connector 28. The output analog signal represents a partially beamformed signal in one embodiment, but may represent a signal from a single element in other embodiments. The signal is output for a single receive beamformer channel of the ultrasound imaging system 14 for complete beamforming of the signals from the various digital-to-analog converters 47. In one embodiment, each digital-to-analog converter 47 is a single device, but a package or chip including a plurality of digital-to-analog converters 47 may be used. In one embodiment, the digital-to-analog converters 47 are included in the same application specific integrated circuit as the combiner 38, but separate devices may be provided.

In the embodiment shown in FIG. 4, the signal processing device 35 is provided at least partially within the connector housing 20. Since analog-to-digital converters 36 are provided within the transducer assembly, the wires of the cable 18 may be matched in length and impedance. The cable 18 is of a known length for every channel, allowing a signal bandwidth in multiplexing rates to be maximized. The electronics allow the sub-arrays to be beamformed using fixed delays, dynamic delays, correlation, frequency or other techniques available for digital processing whether now known or later developed. By combining signals from different elements into different sub-arrays or altering the partial beamforming, different transducer designs may be used with the same or different receive beamformers 26. For example, a two-dimensional array is provided with 1,728 elements. For operation with 192 receive beamformer channels, groups of 3×3 elements are partially beamformed. Since the partial beamforming matches the number of sub-arrays to the number of receive beamformer channels, ultrasound systems 14 with a higher number of receive beamformer channels may use smaller sub-arrays, and systems with a lower number of channels may use larger sub-arrays. Programmable signal processing also allows selection of different shapes of sub-arrays, such as changing or steering using the sub-array shape. The sub-array configuration may be dynamic in size, shape and location as a function of depth. In further embodiments, amplifiers are provided for applying apodization to signals from individual elements prior to partial beamforming or for applying apodization after partial beamforming. Providing programmable sub-arrays also allows a tradeoff between the sizes of the sub-array or partial beamforming and a number of different beams received simultaneously in response to the same transmit event. For example, a receive beamformer 26 with 256 channels may divide the channels in half, with each half receiving the same combination of 128 sub-arrays for forming two parallel receive beams. The focusing applied to the sub-arrays or partial beamforming is a compromise between the two receive beams, independent of the steering direction or based on the steering direction of one of the two receive beams.

The detachable connector 28 electrically connects with the ultrasound transducer array 32 without any detachable connections. Alternatively, one or more detachable connections is provided, such as at the interface between the cable 18 and the probed housing 16. The connector 28 is releasably connectable and disconnectable with the ultrasound system 14. The connector 28 includes mechanical and electrical structures corresponding to the mechanical and electrical structures of the connector 22 of the ultrasound system 14. For example, a plurality of electrical signal lines for connection with exposed traces on a circuit board protrudes from the connector housing 20 for insertion into the connector 22. In one embodiment, the connector 28 is a connector as disclosed in U.S. Pat. No. 6,371,918. Different connectors may be provided. Latches, extensions, screws, threaded holes or other now-known or later-developed releasable connection structures are provided for mechanically attaching the connectors 28 and 22. The connectors 28 and 22 are operable to easily detach and attach. Through rotation, latching or other processes, the connectors 22, 28 are attached or detached in seconds or tens of seconds. Longer time periods may be used for more solid connections or for different connectors.

The connectors 22, 28 include power, clock, synchronization or other control lines for implementing the digital processing within the connector housing 20 or the transducer assembly 12 in synchronization with a format usable by the ultrasound system 14. Electrical outputs or connections are provided for each of the outputs or signals representing different elements or groups of elements of the array 32 as processed by the signal processing device 35. For example, the detachable connector 28 has a plurality N of outputs. N is less than the number of elements of the array 32 in one embodiment, but may be equal or more in other embodiments.

Different signal processing of information from the elements of the array 32 is used in other embodiments. In the embodiment shown in FIG. 4, the analog signals are converted to digital signals, digital partial beamforming is provided and then the partially beamformed signals are converted to analog signals within the transducer assembly. In other embodiments, the analog signals are converted to digital signals within the probe housing 16 and digital communication is provided, such as wireless, fiber optic or other electrical trace from the probe housing 16 to the connector housing 20. Partial digital beamforming and/or digital-to-analog conversion are performed in the connector housing 20. While time division multiplexing is discussed above, frequency division multiplexing or other spread spectrum techniques may be used. For example, frequency multiplexed signals are demultiplexed and time delay beamforming is performed within the connector housing 20. For an example using code division multiplexing, the signals are demultiplexed and a delay and sum beamformer is provided within the connector housing 20. Any of the signal processes discussed above or other signal processes may be provided, including processing other than partial beamforming or format conversion.

In one embodiment, the signal processing device 35 of the transducer assembly 12 performs a set function. Alternatively, the signal processing device 35 is programmable. For example, different steering angles are programmed for implementing different partial beamforming schemes. A data interface is provided between the ultrasound system 14 and the signal processing device 35, such as a data interface provided through the connectors 22, 28. A clock signal is also provided through the connectors 22, 28 for beamforming, but an independent clock may be used in other embodiment. By using a same clock signal, the transducer probe 12 is synchronized with the ultrasound system 14. The connectors 22, 28 also provide power to the transducer assembly 12. In other embodiments, a battery or other source of power is provided.

Figure 5:
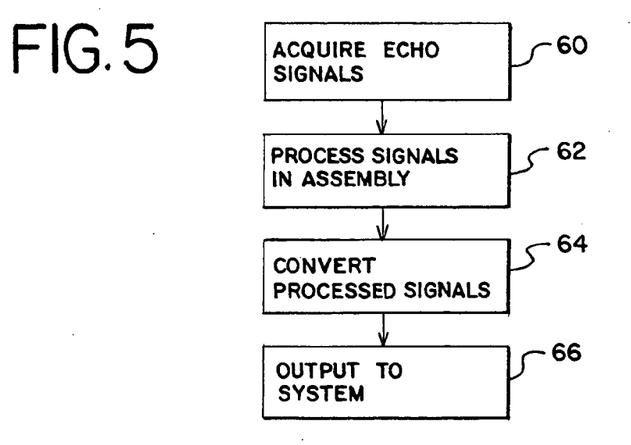
FIG. 5 is a flowchart diagram of one embodiment of a method for adapting signals from an ultrasound transducer for an ultrasound system.

FIG. 5 shows one embodiment of a method for adapting signals from an ultrasound transducer for an ultrasound system. The adaptation is performed within a transducer assembly to convert signals for compatibility with the ultrasound system. For example, the images generated by the ultrasound system may be undesirable, noisy or otherwise unusable due to a difference in the. signals within the transducer assembly 12 from a form expected by the ultrasound system. The ultrasound system may be incapable of forming beams without the signals being altered for compatibility. Different signal spaces are provided and are not compatible, such as signals with altered spectral content, analog as opposed to digital or at different frequencies. Translation or conversion hardware is positioned within the transducer assembly, such as along the cable or within a connector housing. The conversion hardware is spaced from the transducer probe in one embodiment, but may be positioned within the transducer probe in other embodiments. While four acts are shown in FIG. 5 for adapting signals from a transducer to a system, different, additional or fewer acts may be provided in other embodiments. The method of FIG. 5 is implemented using the systems discussed above with respect to FIGS. 1 through 4 or other systems.

In act 60, echo signals are acquired. The echo signals are required at each of a plurality of elements. For example, echo signals are acquired for each element of a two-dimensional array for real time three-dimensional imaging. In alternative embodiments, the echo signals are acquired from sparse sampling of the array or from other sources, such as through digital transmission from a remote transducer.

In act 62, the signals from a plurality of elements are processed within the transducer assembly. For example, the signals are processed within a transducer probe housing, a connector housing, along a cable spaced away from the probe housing or combinations thereof. Signals processed are from at least one element. In one embodiment, the signals from a plurality of elements of a multidimensional array are processed. Any of various signal processing may be used, such as filtering, remapping, conversion or partial beamforming.

In one embodiment, the signals from a plurality of elements are partially beamformed into a fewer number of processed signals. For example, signals from 1,728 elements are partially beamformed onto 192 signals each representing a different sub-array or sub-aperture of elements. By partially beamforming the signals from a plurality of elements in the transducer assembly, ultrasound imaging systems with a fewer number of receive channels may be used. In one embodiment, the number of elements is two or more times as large as the number of receive beamformer channels. By partially beamforming, signal information from each of the elements is maintained but output along fewer signal lines for use by the receive beamformer. Other ratios may be provided, such as greater than a multiple of 2 or less than a multiple of 2.

In one embodiment, the signal processing is partial beamforming using sub-array mixing. For each sub-aperture, different phase shifts are applied to signals from different elements by mixing with a signal having the same or different frequency. The signals within the sub-aperture are then combined. The phase shifts act as delays for implementing delay and sum type beamforming. Additional signal processing may be provided, such as conversion of the sub-array mixed partially beamformed signals to a form compatible with or more appropriate for the receive beamformer. In one embodiment, the sub-array mixing is performed within the transducer probe housing, but may be performed elsewhere within the transducer assembly.

In another embodiment, the signals are processed using multiplexing. The signals from a plurality of elements are multiplexed onto a same signal line, such as using time division multiplexing for each of a plurality of sub-apertures. In one embodiment, the multiplexing is performed adjacent to the transducer in the transducer probe housing, but may be performed elsewhere in the transducer assembly. The signals are then demultiplexed elsewhere within the transducer probe assembly, such as within a connector housing. The demultiplexing provides signals for each of the elements. To reduce the number of signals for real time three-dimensional imaging, partial beamforming is then provided on the demultiplexed signals. Partial beamforming is performed in the analog or digital domain.

Other signal processing may be provided. The signal processing alters the data from the elements of the transducer array. The data may be altered to be incompatible in some way with the receive beamformer or desired imaging for some signal processing. For example, the spectral content of the signals is flipped or mirror imaged, the receive beamformer is inoperable to use multiplexed data, or the receive beamformer is inoperable to use digital or analog data.

In act 64, the processed signals are further signal processed by conversion to a different form appropriate for the ultrasound system. The conversion is performed within the transducer assembly, such as within the connector housing that is releasable from the ultrasound system. The conversion may be performed in other locations, such as within the cable 18 or within the probe housing in other embodiments. Any of various conversions may be used, such as analog-to-digital conversion, digital-to-analog conversion, up-converting, down-converting, filtering, multiplexing, demultiplexing, multiplying, summing, subtracting, dividing, or other now known or later developed processes for altering analog or digital data. In one embodiment, partially beamformed signals are converted to a different form appropriate for the ultrasound system. For example, partially beamformed signals are mixed to shift from an intermediate frequency to a radio frequency. Where the beamformer is compatible with input signals within a certain frequency range, the mixing shifts the signals to within the frequency range. The mixing may alternatively or additionally alter the spectral content of the signals. In the time division multiplexing embodiment of FIG. 4, the conversion is demultiplexing and/or conversion of digital signals to analog signals.

In act 66, the converted signals are output. For example, partially beamformed converted signals are output to a plurality. of beamformer channels where the number of beamformed channels is less than the number of elements. By performing the partial beamforming and conversion within the transducer assembly, a multidimensional array may be used for scanning a patient while imaging is provided using a conventional ultrasound system with a lesser number of receive channels. As a result, real time three-dimensional imaging is more likely possible. By converting processed signals and outputting the converted signals within the detachable connector housing of a transducer assembly, any advantages associated with processing or transmitting data in forms different than compatible with the receive beamformer may be used within the transducer assembly. For example, time division multiplexing or sub-array mixing are used prior to conversion and output for minimizing the number of signal lines or cables between the transducer probe and the connector housing.

Other embodiments are disclosed in U.S. Pat. No. 7,998,072(application Ser. No. 10/741,827(Attorney Reference Number 2003 P14534)), the disclosure of which is incorporated herein by reference. Partial beamforming, conversion of data and other signal processing and related structures are shown in yet another configuration in the transducer assembly.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for adapting signals from an ultrasound transducer for an ultrasound system, the method comprising:
   (a) processing signals from a plurality, M, of elements within a transducer assembly having a transducer connector releasably connectable with the ultrasound system, the ultrasound system comprising a transmit beamformer, a receive beamformer, and a system connector in a system housing, the system housing comprising a cart-based housing resting on wheels, the system connector permanently connected through a transmit and receive switch to the transmit and receive beamformers; and
   (b) converting the processed signals to a different form appropriate for the ultrasound system, the conversion being in the transducer assembly;
   wherein (a) comprises processing signals for a given range from the plurality, M, of elements of a multi-dimensional array of the elements to a lesser plurality, N, of processed signals;
   wherein (a) comprises processing within a transducer probe housing, the transducer probe housing being shaped for handheld use, and wherein (b) comprises converting within a connector housing releasable from the ultrasound system, the converting making signals, from the elements, in the connector housing compatible with the receive beamformer;
   further comprising connecting, with a cable, the transducer probe housing with the connector housing, the connector housing at least partially enclosing the transducer connector, the transducer connector releasably connectable with the system connector; and
   transmitting the signals from the elements to the connector housing.

2. The method of claim 1 wherein (a) comprises partially beamforming signals for each of a plurality of sub-apertures.

3. The method of claim 2 wherein (a) comprises for each sub-aperture:
   (a1) applying different phase shifts to signals from different elements; and
   (a2) combining the signals.

4. The method of claim 1 wherein (a) comprises partially beamforming demultiplexed signals.

5. The method of claim 1 wherein (b) comprises converting digital signals to analog signals.

6. The method of claim 1 wherein (b) comprises mixing the signals.

7. A transducer assembly for adapting signals from an ultrasound transducer for an ultrasound system, the assembly comprising:
a transducer probe housing including the ultrasound transducer;
a cable connected with the ultrasound transducer; and
a connector housing at least partially enclosing a detachable connector and a signal processing device, the cable electrically connecting elements of the ultrasound transducer to the signal processing device, the cable external to the connector housing between the ultrasound transducer and the connector housing, and the detachable connector operable to connect and disconnect from the ultrasound system and operable to output signals responsive to the signal processing device and the ultrasound transducer;
wherein the signal processing device comprises a partial beamformer;
the transducer assembly configured for connection with the ultrasound system comprising a cart-based system, the connection being standardized for the cart-based system such that different transducer assemblies, including the transducer assembly, are connectable with the cart-based system for different examinations, the output signals of the transducer including signals in a plurality of channels for receive beamformation by the cart-based system.

8. The assembly of claim 7 wherein the ultrasound transducer comprises a multidimensional array of M elements and the detachable connector having a plurality N of outputs for the output signals, M being greater than N.

9. The assembly of claim 7 wherein the signal processing device comprises a digital-to-analog converter.

10. The assembly of claim 7 wherein the signal processing device comprises a mixer.

11. The assembly of claim 7 wherein the signal processing device comprises a demultiplexer.

12. The assembly of claim 7 wherein the signal processing device is operable to convert the processed signals to a different form appropriate for the ultrasound system.

13. A method for adapting signals from an ultrasound transducer for an ultrasound system, the method comprising:
(a) partially beamforming signals from a plurality, M, of elements of the ultrasound transducer, the partial beamforming being performed in a transducer probe housing of a transducer assembly;
(b) converting the partially beamformed signals to a different form appropriate for the ultrasound system, the conversion being performed in a connector housing releasable from the ultrasound system, the connector housing part of the transducer assembly and connected to the transducer probe housing by a cable, the cable comprising at least sixty four coaxial cables external of the connector housing and a probe housing enclosing the elements; and
(c) outputting the converted, partially beamformed signals to a plurality, N, of beamformer channels of the ultrasound system, N being less than M, the ultrasound system comprising a cart-based system having a receive beamformer for receiving the partially beamformed signals on the beamformer channels.

14. The method of claim 13 wherein (a) comprises sub-array mixing and (b) comprises mixing to a frequency of the beamformer channels.

15. The method of claim 13 further comprising:
(d) multiplexing the signals from the plurality of elements adjacent a transducer probe; and
(e) demultiplexing the signals within the connector housing;
wherein (b) comprises converting digital signals to analog signals.

16. The method of claim 13 wherein (b) and (c) are performed with at least one signal processing device in the connector housing of the transducer assembly.

17. The method of claim 13 wherein (a) comprises partially beamforming from M signals to N signals, M being at least a multiple of two of N.

18. The method of claim 13 wherein (a) comprises partially beamforming for at least two simultaneously received beams.

19. A method for adapting signals from an ultrasound transducer for an ultrasound system, the method comprising:
(a) processing signals from a plurality of elements within a transducer housing; and
(b) further processing the signals sent from the transducer housing to a detachable connector within a detachable connector housing, the detachable connector housing spaced from the transducer housing by an external cable, the transducer housing, external cable, and detachable connector housing comprising a transducer assembly for connection to the ultrasound system, the ultrasound system being cart-based and connectable to different transducer assemblies, including the transducer assembly, for receiving data in a standard format, the signals received in the detachable connector housing resulting from the processing of (a) resulting in signals incompatible with the standard format;
wherein (b) comprises one of:
(b1) digital-to-analog converting of the signals; and
(b2) mixing the signals.

20. The method of claim 19 wherein (b) comprises converting the processed signals of (a) to a different form appropriate for the ultrasound system.

21. The method of claim 19 wherein (a) comprises partially beamforming signals for each of a plurality of sub-apertures.

* * * * *